United States Patent
Schnaibel et al.

(10) Patent No.: US 6,436,277 B2
(45) Date of Patent: Aug. 20, 2002

(54) ELECTROCHEMICAL SENSOR

(75) Inventors: Eberhard Schnaibel, Hemmingen; Harald Neumann, Vaihingen; Johann Riegel, Bietigheim-Bissingen; Lothar Diehl, Stuttgart, all of (GB)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/247,737

(22) Filed: Feb. 9, 1999

(30) Foreign Application Priority Data

Feb. 9, 1999 (DE) .......................... 198 05 023

(51) Int. Cl.[7] .......................................... G01N 27/407
(52) U.S. Cl. .................... 205/784; 204/425; 204/426; 204/429
(58) Field of Search ..................... 204/421–429; 205/783.5, 784, 784.5, 785

(56) References Cited

U.S. PATENT DOCUMENTS

| | | | |
|---|---|---|---|
| 4,177,112 A | * 12/1979 | Suzuki et al. | 204/429 |
| 4,272,349 A | * 6/1981 | Furutani et al. | 204/429 |
| 4,402,820 A | * 9/1983 | Sano et al. | 204/429 |
| 4,502,939 A | * 3/1985 | Holfelder et al. | 204/427 |
| 4,798,693 A | * 1/1989 | Mase et al. | |
| 4,859,307 A | * 8/1989 | Nishizawa et al. | |
| 4,943,330 A | * 7/1990 | Iino et al. | |
| 5,314,604 A | * 5/1994 | Friese et al. | 204/426 |
| 5,676,811 A | * 10/1997 | Makino et al. | 204/425 |
| 6,007,688 A | * 12/1999 | Kojima et al. | 204/427 |

* cited by examiner

Primary Examiner—T. Tung
(74) Attorney, Agent, or Firm—Kenyon & Kenyon

(57) ABSTRACT

An electrochemical sensor for ascertaining a gas concentration of a measuring gas includes an electrochemical element, including a first solid electrolyte body having an electrochemical pump cell and a first and a second electrode, and having a gas compartment which is connected via a gas access opening to the measuring-gas compartment, and in which one of the two electrodes is arranged. The electrochemical element further includes a second solid electrolyte body having an electrochemical sensor cell (Nernst cell) and a third and a fourth electrode. The surface of the first solid electrolyte body faces the measuring-gas compartment, and the gas access opening is covered by a porous protective layer. The electrochemical sensor includes a layer that exhibits a higher density or a lower porosity compared to the protective layer and that is allocated to the porous protective layer.

13 Claims, 2 Drawing Sheets

ELECTROCHEMICAL SENSOR

FIELD OF THE INVENTION

The present invention relates to a sensor, in particular an electrochemical sensor.

BACKGROUND INFORMATION

Known electrochemical sensors include an electrochemical element, which has an electrochemical pump cell having a preferably planar, first solid electrolyte body and a first and a second preferably porous electrode. Moreover, these sensors include an electrochemical sensor cell, interacting with a pump cell, having a preferably planar, second solid electrolyte body and a third and a fourth preferably porous electrode. This sensor further includes a gas access opening and a gas access channel, so that an inner hollow space, also called a gas compartment, is connected to a measuring-gas compartment. Arranged in the hollow space, which is formed by a recess in at least one of the solid electrolyte bodies, is a diffusion resistance device which can include a porous filling. Thus, the measuring gas arrives in the gas compartment via the gas access opening and the gas access channel, the first and the second electrode of the pump cell acting so as to regulate the admission of the measuring gas into the gas compartment, and thus assuring a controlled partial pressure of the gas component to be measured. The electrochemical potential difference between the third and the fourth electrode of the second solid electrolyte body arises because of the different partial gas pressures in the diffusion resistance device, as well as in a reference-gas compartment required, for example, in the second solid electrolyte body. This potential difference can be detected by a voltmeter situated outside of the electrochemical element.

It has also been suggested to cover the gas access opening with a porous covering to prevent liquid constituents which can be contained in the measuring gas (e.g. gasoline) from penetrating into the interior of the sensor, thus essentially into the gas compartment. This covering is a porous layer on the surface of the electrochemical element facing the measuring-gas compartment. The covering is penetrable by the measuring gas, but represents a barrier for liquid constituents contained in the measuring gas. The stored-up liquid, held back in the covering, evaporates quickly after a provided heating device switches on. The porous covering is arranged on the outer pump electrode and is made, for example, of $ZrO_2$. This covering can contain platinum, and can make oxygen from the measuring gas available for the pumping. Moreover, this covering is intended, on the one hand, to prevent soiling of the outer pump electrode, and on the other hand, to form the already mentioned barrier for the liquid constituents in the measuring gas.

Nevertheless, the measuring gas, which is not greatly hindered by this protective layer, passes through the protective layer quickly, and thus arrives at the outer pump electrode. This means that, with the changing gas composition of the measuring gas, the gas atmosphere at the outer pump electrode can also change very quickly. Consequently, the vacancy concentration at the electrode, and thus the internal resistance of the pump cell, also changes. However, depending on the energy supply (current or voltage source) of the pump cell, the pump current will then also change immediately, even before the gas composition in the hollow space of the sensor has newly adjusted. Thus, the gas adjustment in the gas compartment lags behind the gas adjustment at the outer pump electrode. This interrelation causes the known, but unwanted, phenomenon of the lambda=1 ripple (the output signal manifesting counter- or overshoot-oscillation in response to an abrupt gas exchange).

Sensors of the type described above, under the technical designation of planar wideband-lambda probes, have been used, for example, in the technology of catalytic exhaust emission control of internal combustion engines.

SUMMARY OF THE INVENTION

The present invention makes available an electrochemical sensor for ascertaining a concentration of gas, e.g., a concentration of oxygen, in a measuring gas, the sensor having an electrochemical element. The sensor includes a first solid electrolyte body having an electrochemical pump cell, which has a first and a second electrode. The sensor furthermore has a gas compartment, which is connected via a gas access opening to the measuring-gas compartment, and in which one of the two electrodes is arranged. In addition, the sensor has a second solid electrolyte body having an electrochemical sensor cell (Nernst cell), which includes a third and a fourth electrode. The surface of the first solid electrolyte body facing the measuring-gas compartment and the gas access opening are covered by a porous protective layer. The electrochemical sensor of the present invention has the particular feature that a layer, which exhibits a higher density, i.e., a lower porosity compared to the protective layer, is allocated to the porous protective layer. Because a protective layer having a higher density or lower porosity is provided, the access of the measuring gas to the outer pump electrode is delayed. This has the advantage that the pump current first changes when the measuring gas has also reached the hollow space, thus the gas compartment. In this manner, the "lambda=1 ripple" is prevented. It is thus ensured that the access of the measuring gas to the outer pump electrode does not take place substantially earlier than to the inner pump electrode, thus to the second electrode and to the third electrode.

One preferred exemplary embodiment has the feature that the layer and the protective layer exhibit the same density or porosity. Thus, a single layer is formed which quasi performs a double function. On the one hand, the protective layer prevents liquid constituents contained in the measuring gas from penetrating into the gas compartment. On the other hand, the delayed access of the measuring gas to the first electrode (outer pump electrode) is achieved. In addition, this layer has the function of preventing the ageing of electrodes caused by exhaust gas components.

Alternatively, in a further exemplary embodiment, a gas-tight covering layer, for example, a layer made of $ZrO_2$, can be arranged on the protective layer, thus facing the measuring-gas compartment. In a preferred specific embodiment, the layer has a thickness which can amount to 20 $\mu$m. In this case, the protective layer can have a lesser density than the gas-tight covering layer.

Dense-sintering zirconium dioxide is preferred as material for the structure of the layer and/or the protective layer of the sensor according to the present invention. Alternatively, it is possible to use aluminum oxide ($Al_2O_3$), which is nanocrystalline, and therefore dense-sintering.

The gas access opening can be connected to a gas access channel which is formed, at least partially, as a hollow space, and which can be filled with a porous filling. This hollow space prevents capillary passing-on of liquid such as gasoline to the inner porous filling. The hollow space can be produced by burning off sublimable material during the sintering process.

The gas access opening can be covered by a porous covering. This covering is preferably formed from a porous material that can be the continuation of the porous protective layer which overlays the surface of the electrochemical element facing the measuring-gas compartment.

According to a variant of the present invention, the porous filling usually provided in the gas compartment is omitted. Consequently, the diffusion barrier is eliminated, and the access of the measuring gas to the second and the third electrode within the gas compartment is accelerated, so that the equally rapid adjustment of the composition of the measuring gas at all three electrodes (first to third) can be achieved in this manner, as well.

Electrochemical sensors according to the present invention and their electrochemical elements are expediently manufactured by beginning with plate-like or foil-type oxygen-conducting solid electrolytes made, for example, of stabilized zirconium dioxide, and coating them on both sides with, in each case, an inner and outer pump electrode having the necessary printed circuit traces. In this context, the inner pump electrode is located advantageously in the edge area of a diffusion or gas access channel, through which the measuring gas is supplied, and which functions as the gas diffusion resistance. The pump cell obtained in this manner can then be laminated together with a sensor cell (Nernst cell), produced in a similar manner, composed of a second solid electrolyte foil and a third solid electrolyte foil, possibly constructed to form a heater unit, and be sintered, for example, at 1300 to 1550° C.

For manufacturing the porous fillings, one begins, for example, from porously sintering foil inserts made of a ceramic material having suitable thermal expansion properties that correspond or come close to those of the solid electrolyte foils used. Advantageously used for the filling is a foil insert made of the ceramic material from which the solid electrolyte foils are also made, it being possible to produce the porosity of the insert using pore-forming materials such as thermal carbon black powder, organic plastics, or salts which burn, decompose, or evaporate during the sintering process. The starting materials are used in such quantitative proportions that porosities of 10 to 50% are yielded after sintering, the average pore diameter being approximately 5 to 50 $\mu$m.

The present invention offers the advantage that the gas access from the measuring-gas compartment to the outer pump electrode is delayed compared to known devices, to the extent that the gas access to the outer pump electrode does not take place substantially earlier than to the inner pump electrode ("second") or to the Nernst electrode ("third"), but rather that the measuring gas generally reaches the second and the third electrode sooner or at the same time as the outer pump electrode ("first"). Thus, the disadvantages of the related art, which, for example, lie in the restricted control dynamics of wideband-lambda probes caused by a strong lambda ripple, are overcome.

In a particularly advantageous manner, the present invention relates to wideband-lambda probes for ascertaining the $\lambda$ value of gas mixtures in internal combustion engines. In this context, the $\lambda$ value or the "air number" is defined as the relationship of the prevailing air-fuel ratio to the stoichiometric air-fuel ratio. The probes measure the oxygen content of the exhaust gas on the basis of a change in the limiting current.

DETAILED DESCRIPTION

Figure 1:
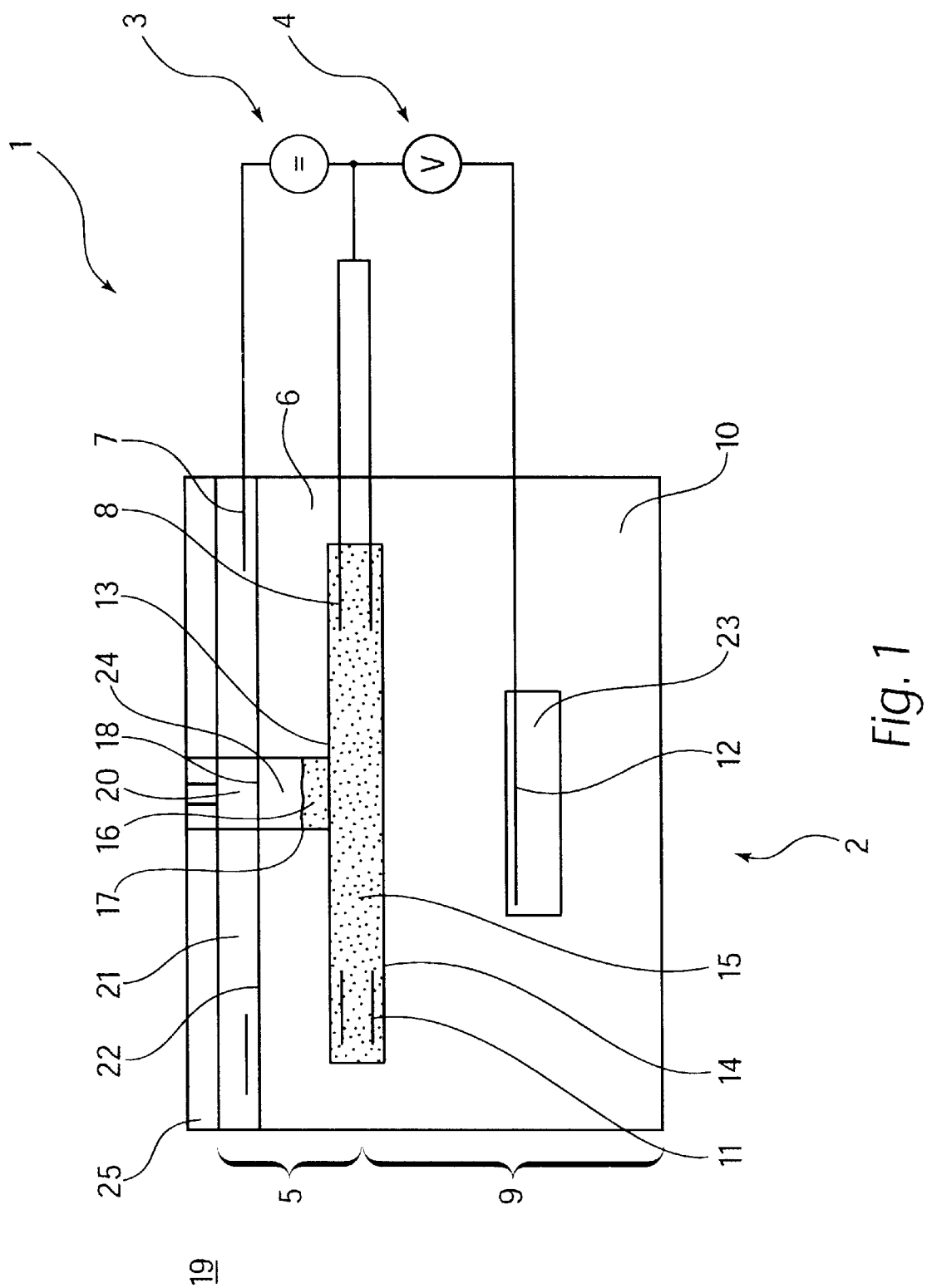
FIG. 1 shows a first exemplary embodiment of an electrochemical sensor.

FIG. 1 shows in cross-section an electrochemical sensor 1, including an electrochemical element 2, a current- or voltage-supply device 3, as well as a voltmeter 4. Electrochemical element 2 has an electrochemical pump cell 5 which is composed of a first planar solid electrolyte body 6, a first porous electrode 7, and a second porous electrode 8. The electrochemical element, hereinafter designated simply as element 2, furthermore has an electrochemical sensor cell (Nernst cell) 9, which is composed of a second solid electrolyte body 10 as well as a third electrode 11 and a fourth electrode 12. Pump cell 5 is supplied with voltage at first and second electrode 7, 8 by external voltage-supply device 3. First and second solid electrolyte bodies 6, 10 are joined to each other and surround an inner hollow space 14 which is also designated as gas compartment 13. The hollow space 14 can be completely filled with a porous material 15 and contains second and third electrodes 8, 11. Inner hollow space 14 is connected to measuring-gas compartment 19 via a gas access channel 17 which is partially filled with a porous filling 16. Placed over gas access opening 18 is a covering 20, which can be part of a porous protective layer 21 that covers a surface 22 of first solid electrolyte body 6 facing measuring-gas compartment 19, and thus covers first electrode 7 of pump cell 5, as well.

Second solid electrolyte body 10 has a reference-gas compartment 23. Disposed in this compartment is fourth electrode 12 which is exposed to a comparison gas, also designated as a reference gas. The measuring gas from measuring-gas compartment 19 reaches inner hollow space 14 via gas. access opening 18 and gas access channel 17, a controlled partial pressure being adjusted, with the assistance of a pump voltage applied to first and second electrodes 7,8 of pump cell 5, by pumping oxygen in or out.

Because of the different partial gas pressures in gas compartment 13 and in reference-gas compartment 23 disposed in second solid electrolyte body 10, an electrochemical potential difference arises between third and fourth electrodes 11, 12 of second solid electrolyte body 10, the difference being detected by voltmeter 4 situated outside of the electrochemical element 2. Naturally, provision can also be made for an evaluator which determines the potential difference.

Covering 20 and hollow space 24 located under covering 20 prevent liquid constituents such as gasoline contained in the measuring gas from penetrating via gas access opening 18 and gas access channel 17 into gas compartment 13. Covering 20 is designed as part of porous protective layer 21, which is disposed on surface 22 of first solid electrolyte body 6 facing measuring-gas compartment 19.

In the exemplary embodiment according to FIG. 1, a layer 25, whose thickness is preferably 20 $\mu$m, is disposed on the side of protective layer 21 facing measuring-gas compartment 19. This layer 25 exhibits a higher density or lower porosity compared to protective layer 21. This ensures that the access of the measuring gas from measuring-gas compartment 19 is delayed, so that the measuring gas is delayed in reaching first electrode 7, also designated as outer pump electrode. That means that the gas access to electrode 7 does not take place substantially earlier than to second electrode 8, also designated as inner pump electrode. In this context, layer 25, or rather its density, can be so selected that the gas access to first electrode 7 takes place essentially simultaneously with the gas access at second electrode 8. In this manner, the lambda=1 ripple is substantially avoided, or even totally prevented.

In a preferred specific embodiment, layer 25 is formed by a density-sintered zirconium dioxide layer.

Thus, layer 25 completely covers protective layer 21. However, provision can also be made for layer 25 to have an opening, so that covering 20 of gas access opening 18 is not covered.

Figure 2:
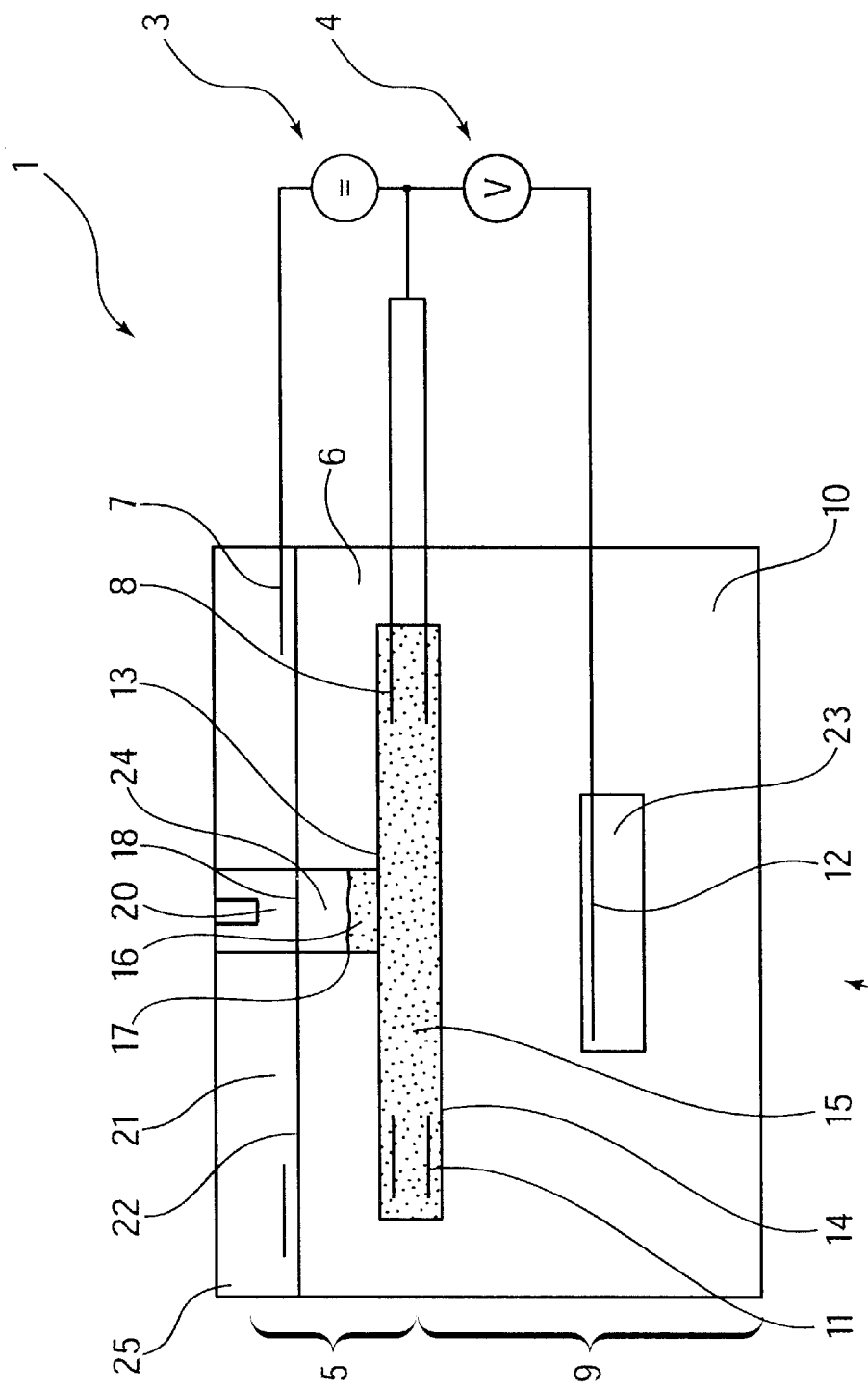
FIG. 2 shows a second exemplary embodiment of an electrochemical sensor.

FIG. 2 shows a second exemplary embodiment of element 2. This embodiment differs from the exemplary embodiment according to FIG. 1 only in that layer 25 is a component of protective layer 21. In this case, provision can be made in particular for protective layer 21 and layer 25 to be made of the same material, e.g., zirconium dioxide. Protective layer 21 and layer 25 in this exemplary embodiment have the same density or porosity, which preferably corresponds to that of layer 25 in the first exemplary embodiment. Thus, density-sintered zirconium dioxide can be provided. So that the gas access to first electrode 7 is not excessively delayed, the thickness of layer 25 or protective layer 21 can be varied. In the exemplary embodiment according to FIG. 2, layer 25 or protective layer 21 assumes several functions. On the one hand, layer 25 or protective layer 21 forms a barrier for liquid constituents contained in the measuring gas. On the other hand, layer 25 or protective layer 21 makes possible the delayed gas access to first electrode 7. Finally, layer 25 or protective layer 21 prevents the ageing of electrodes caused by exhaust gas components.

What is claimed is:

1. An electrochemical sensor for ascertaining a gas concentration of a measuring gas, comprising:
   an electrochemical element including:
      a first solid electrolyte body constituting an electrochemical pump cell with a first electrode, a second electrode, and a gas compartment, which is connected via a gas access opening to a measuring-gas compartment outside of the electrochemical element and in which the second electrode is arranged, wherein the first electrode being arranged on the surface of the first solid electrolyte body that faces the measuring-gas compartment and being covered by a porous protective layer, and
      a second solid electrolyte body constituting an electrochemical sensor cell with a third electrode, and a fourth electrode, wherein the porous protective layer is under a layer having a lower porosity than the protective layer, the lower porosity layer having an opening over the gas access opening so that the gas access from the measuring-gas compartment through the low porosity layer and the protective layer to the first electrode takes place in approximately the same amount of time as the gas access from the measuring-gas compartment to the second electrode.

2. The electrochemical sensor according to claim 1, wherein the electrochemical sensor cell includes a Nernst cell.

3. The electrochemical sensor according to claim 1, wherein:
   the layer is arranged on the protective layer, and
   the layer faces the measuring-gas compartment.

4. The electrochemical sensor according to claim 1, wherein the layer is formed from zirconium dioxide.

5. The electrochemical sensor according to claim 4, wherein at least one of the protective layer and the layer includes a porous covering.

6. The electrochemical sensor according to claim 1, wherein the gas access opening is in communication with a gas access channel formed at least partially as a hollow space.

7. The electrochemical sensor according to claim 6, further comprising a porous filling for at least partially filling the gas access channel.

8. The electrochemical sensor according to claim 1, further comprising a porous filling for at least partially filling the gas compartment.

9. The electrochemical sensor according to claim 1, wherein the gas compartment does not contain a porous filling.

10. The electrochemical sensor according to claim 1, wherein:
    the second solid electrolyte body includes an inner reference-gas compartment for containing a comparison gas, and
    the fourth electrode is exposed to the comparison gas.

11. The electrochemical sensor according to claim 1, wherein
    the gas compartment is formed as an inner hollow space enclosed by the first solid electrolyte body and the second solid electrolyte body, and
    the gas compartment is at least partially filled with a porous filling.

12. The electrochemical sensor according to claim 1, wherein a thickness of the layer is 20 $\mu$m.

13. A method of ascertaining a gas concentration of a measuring gas, comprising the steps of:
    providing an electrochemical element including:
       a first solid electrolyte body constituting an electrochemical pump cell with a first electrode, a second electrode and a gas compartment, which is connected via a gas access opening to measuring-gas compartment outside of the electrochemical element and in which the second electrode is arranged, wherein the first electrode being arranged on the surface of the first solid electrolyte body that faces the measuring-gas compartment, and being covered by a porous protective layer, and a second solid electrolyte body constituting an electrochemical sensor cell with a third electrode and a fourth electrode, wherein the porous protective layer is under a layer having a lower porosity than the protective layer, the lower porosity layer having an opening over the gas access opening so that the gas access from the measuring-gas compartment through the low porosity layer and the protective layer to the first electrode takes place in approximately the same amount of time as the gas access from the measuring-gas compartment to the second electrode; and
    ascertaining a $\lambda$ value of a gas mixture in an internal combustion engine using the electrochemical element.

* * * * *